(12) United States Patent
Vaccaro et al.

(10) Patent No.: US 10,105,296 B2
(45) Date of Patent: *Oct. 23, 2018

(54) THIN FILM TOOTHPASTE STRIP

(71) Applicant: Rita Vaccaro, Englewood Cliffs, NJ (US)

(72) Inventors: Rita Vaccaro, Englewood Cliffs, NJ (US); Babak Ghalili, New York, NY (US); George Anastassov, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/109,313

(22) PCT Filed: Dec. 31, 2014

(86) PCT No.: PCT/US2014/073012
§ 371 (c)(1),
(2) Date: Jun. 30, 2016

(87) PCT Pub. No.: WO2015/103400
PCT Pub. Date: Jul. 9, 2015

(65) Prior Publication Data
US 2016/0324739 A1 Nov. 10, 2016

Related U.S. Application Data

(63) Continuation-in-part of application No. 14/145,267, filed on Dec. 31, 2013, now Pat. No. 9,656,102, which is a continuation of application No. 13/868,445, filed on Apr. 23, 2013, now abandoned.

(51) Int. Cl.
| | |
|---|---|
| A61Q 11/00 | (2006.01) |
| A61K 8/21 | (2006.01) |
| A61K 8/69 | (2006.01) |
| A61K 6/00 | (2006.01) |
| A61K 8/73 | (2006.01) |
| A61K 8/46 | (2006.01) |
| A61K 8/34 | (2006.01) |
| A61K 8/02 | (2006.01) |
| A61C 19/06 | (2006.01) |
| A61C 19/02 | (2006.01) |
| A61K 8/24 | (2006.01) |
| A61K 8/25 | (2006.01) |
| A61K 8/26 | (2006.01) |

(52) U.S. Cl.
CPC .............. *A61K 8/21* (2013.01); *A61C 19/02* (2013.01); *A61C 19/063* (2013.01); *A61K 8/0216* (2013.01); *A61K 8/24* (2013.01); *A61K 8/25* (2013.01); *A61K 8/26* (2013.01); *A61K 8/345* (2013.01); *A61K 8/463* (2013.01); *A61K 8/69* (2013.01); *A61K 8/731* (2013.01); *A61Q 11/00* (2013.01); *A61K 2800/28* (2013.01); *A61K 2800/592* (2013.01)

(58) Field of Classification Search
CPC ............. A61Q 11/00; A61K 8/21; A61K 8/69
See application file for complete search history.

(56) References Cited

U.S. PATENT DOCUMENTS

| | | | |
|---|---|---|---|
| 3,095,356 A | 6/1963 | Moss | |
| 3,122,483 A | 2/1964 | Rosenthal | |
| 3,574,824 A | 4/1971 | Echeandia et al. | |
| 3,669,221 A | 6/1972 | Hase | |
| 3,689,537 A | 9/1972 | Kuder | |
| 3,782,446 A | 1/1974 | Walter | |
| 3,842,168 A | 10/1974 | Colodney | |
| 3,863,006 A | 1/1975 | Hodosh | |
| 3,991,177 A | 11/1976 | Vidra et al. | |
| 4,396,599 A | 8/1983 | Sipos | |
| 4,585,649 A | 4/1986 | Lynch | |
| 4,931,273 A | 6/1990 | Gaffar et al. | |
| 4,986,289 A | 1/1991 | McWhorter | |
| 5,279,815 A | 1/1994 | Wason et al. | |
| 5,292,528 A * | 3/1994 | Mori | A61K 8/416 424/401 |
| 5,374,417 A | 12/1994 | Norfleet et al. | |
| 2006/0134025 A1 | 6/2006 | Trivedi et al. | |
| 2006/0140881 A1 | 6/2006 | Xu et al. | |
| 2008/0171001 A1* | 7/2008 | Engelman | A61K 8/24 424/50 |
| 2009/0060958 A1* | 3/2009 | Mello | A61K 8/02 424/401 |

FOREIGN PATENT DOCUMENTS

WO    WO 9855044 A1 * 12/1998 ........... A61C 19/063

OTHER PUBLICATIONS

International Search Report and Written Opinion of the International Searching Authority, Application No. PCT/US2014/073012, dated Jul. 7, 2015, 10 pages.

* cited by examiner

*Primary Examiner* — Tracy Liu
(74) *Attorney, Agent, or Firm* — Ziegler IP Law Group, LLC

(57) ABSTRACT

The invention relates to rapidly dissolving films and methods of their preparation and administration to a patient. The mono- or multi-layer films contain a water soluble polymer. The films also contain a dentifrice ingredient that is distributed throughout one or more layers of the film.

8 Claims, No Drawings

THIN FILM TOOTHPASTE STRIP

The present application is a national stage filing under 35 U.S.C. § 371 of international application number PCT/US2014/073012, filed 31 Dec. 2014, published on 9 Jul. 2015 as WO 2015/103400, which claims priority to U.S. application Ser. No. 14/145,267 filed 31 Dec. 2013, each of which is incorporated herein by reference in their entirety.

FIELD OF THE INVENTION

The invention relates to rapidly dissolving films and methods of their preparation and administration to a patient. The mono- or multi-layer films contain a water soluble polymer. The films also contain a dentifrice ingredient that is distributed throughout one or more layers of the film.

BACKGROUND

Toothpaste is typically is in the form of a tube containing a gel containing a multiplicity of ingredients. These tubes are heavy, have tendency to leak or dry out if the cap is not secured tightly. Additionally toothpastes contain fluoride compounds that present risks of over delivery of active agent due to the inability to accurately measure and deliver toothpaste portion.

Tooth decay is an infectious, multifactorial disease of global reach. Good dental practices have made a huge impact in reducing risk factors associated with poor dental hygiene. Introduction and acceptance of fluoride has led to a reduction of the incidence of dental caries and has been demonstrated to slow or reverse the progression of existing lesions (i.e., prevents cavities). Fluoride's ability to inhibit or even reverse the initiation and progression of dental caries is well documented. The first use of adjusted fluoride in water for caries control began in 1945 and 1946 in the United States and Canada, when the fluoride concentration was adjusted in the drinking water supplying four communities. The success of water fluoridation in preventing and controlling dental caries led to the development of fluoride-containing products, including toothpaste (i.e., dentifrice), mouthrinse, dietary supplements, and professionally applied or prescribed gel, foam, or varnish. Unfortunately, the success of fluoride use has led to over use in the population. Fluoride intake particularly among children aged 6 years and younger has been on the rise increasing the risk for enamel fluorosis.

Thus there exists a need for an alternative dosage forms to tubes of gel like toothpaste tubes and containers.

SUMMARY

The present invention is directed to a non-adhering oral tape, film or strip home oral care composition comprising a cleansing effective amount of a teeth cleaning agent and a fluoridating effective amount of a fluoridating agent; to methods of forming or using these non-adhering oral tapes, films or strips, and particularly to non-adhering oral tapes, films or strips containing precise dosage amounts of fluoride. Precision fluoride dosage can help mitigate the inherent problems of fluoride over dosage associated with standard dentifrice formulations. The present invention also is directed to kits for home use containing these non-adhering oral tapes, films or strips.

Cleansing and fluoridating effective are terms well known to those skilled in the art and generally refer to improving the surface tone of the teeth by reducing adherent deposits of solid or semisolid nature or increasing the fluoride concentration in the oral environment (preferably within the tooth surface).

In another embodiment the method comprises coating a liner substrate with a wet slurry of film forming ingredients and drying the wet slurry in a drying oven to form a film. Moisture content of the film is measured as the film exits the drying oven and the film is rewound on itself. The rewound film is then stored in a minimal moisture loss environment during a curing process.

In another embodiment the non-adhering oral tape, film or strip non-adhering oral tape, film or strip home oral care composition comprises a cleansing and fluoridating effective amount of a teeth cleaning agent and a fluoridating agent in precise dosage amounts of fluoride.

In another embodiment the non-adhering oral tape, film or strip home oral care composition fluoridating agent is selected from the group consisting of sodium fluoride, potassium fluoride, calcium fluoride, sodium fluorosilicate, sodium monofluorophosphate (MFP), acidulated phosphate fluoride, difluorosilane, ammonium fluorosilicate, stannous fluoride and stannous chloride.

In another embodiment the non-adhering oral tape, film or strip home oral care composition fluoridating agent is present in an amount of 0.01 to 10 weight percent, more particularly less than 5 weight percent.

In another embodiment the non-adhering oral tape, film or strip home oral care composition fluoridating agent is present in an amount of 0.01 mg to 10 mg, more preferably 0.01 to 1 mg. The actual dosage is dependent on the particular fluoride source used. Ideally the fluoride concentration is about 0.004-0.008 mmoles, more preferably 0.006 mmoles. When the fluoride source is sodium fluoride, the preferred dosage is 0.25 mg. Other fluoride sources such as the hexavalent sodium fluorosilicate would be equivalently dosed at about 0.20 mg. Strips comprising 0.01 mg of fluoride are also specifically contemplated as are strips comprising 0.25, 0.5, 0.75 mg, and 1 mg of fluoride, more specifically sodium fluoride. Strips may be perforated unit strips on a roll or individual tabs.

Another embodiment of the non-adhering oral tape, film or strip home oral care composition fluoridating agent is present in an amount appropriate for a child between the ages two (2) to six (6). For children near the lower age a range of 0.01 to 3 weight percent may be appropriate. For children near the older age range five (5) to ten (10) weight percent may be more appropriate. Children in the middle age range 3 to 6, preferably 5, weight percent may be more appropriate. Addition of agents promoting spitting (fiber, fibrillar network, strand, salivary stimulants, and expectorants) can be particularly useful in managing the risk factors associated with children swallowing the fluoride dose. Choice of non-adhering tape to be non-dissolving or partially dissolving can also facilitate the spitting reflect after brushing.

In another embodiment the non-adhering oral tape, film or strip home oral care composition fluoridating agent is present in an amount of 0.01 to 3 percent, more specifically 2 percent sodium fluoride NaF (0.9% [9000 ppm] fluoride). The unit dosage is 0.25 mg In another embodiment the non-adhering oral tape, film or strip home oral care composition fluoridating agent is present in an amount of 3 to 6 percent, more preferably 5 percent sodium fluoride (2.26% [22,600 ppm] fluoride).

In another embodiment the non-adhering oral tape, film or strip home oral care composition fluoridating agent is present in an amount of 6 to 10 percent, more preferably 8 to 9 percent acidulated phosphate fluoride (APF) (1.23% [12,300 ppm] fluoride).

In another embodiment the non-adhering oral tape, film or strip home oral care composition fluoridating agent is present in an amount of 0.5 to 3 percent, more preferably 0.9 percent (%) difluorosilane/polyurethane base (0.1% [1,000 ppm] fluoride).

In another embodiment the non-adhering oral tape, film or strip home oral care composition fluoridating agent is present in an amount of 8,000 to 15000 ppm F.

In another embodiment the non-adhering oral tape, film or strip home oral care composition fluoridating agent sodium fluoride is present in an amount of 9,000 to 12000 ppm F.

In another embodiment the non-adhering oral tape, film or strip home oral care composition fluoridating agent sodium fluoride is present in an amount of 2,000 to 8,000 ppm fluoride.

In another embodiment the non-adhering oral tape, film or strip home oral care composition fluoridating agent sodium fluoride is present in an amount of 3,000 to 5,000 ppm fluoride.

In another embodiment the non-adhering oral tape, film or strip home oral care composition fluoridating agent acidulated phosphate fluoride is present in an amount of 12,300 ppm fluoride.

In another embodiment the non-adhering oral tape, film or strip home oral care composition fluoridating agent difluorsilane is present in an amount of 1,000 ppm fluoride.

In another embodiment the non-adhering oral tape, film or strip home oral care composition cleansing agent is an abrasive agent.

In another embodiment the non-adhering oral tape, film or strip home oral care composition abrasive agent is selected from the group consisting of abrasive silica, sodium metaphosphate, potassium metaphosphate, tricalcium phosphate, dihydrated dicalcium phosphate aluminum silicate, calcined alumina, and bentonite.

In another embodiment the non-adhering oral tape, film or strip home oral care composition cleansing agent is a foaming agent such as sucrose monostearate, sucrose distearate, sulfates such as sodium lauryl sulfate or sodium α-olefinsulfates, N-acylgarcosinates, N-acylglutamates, N-acyltaurates, sucrose fatty acid esters, armalolamnide, polyoxyethylene hydrogenated castor oil, and polyglycerin fatty acid esters and mixtures thereof. The foaming agent is generally present in the composition in an amount from about 4 to about 20 weight percent and, preferably, in an amount from about 7 to about 13 weight percent.

Other embodiments of the invention include the non-adhering oral tape, film or strip home oral care composition cleansing agent is at least one foaming agent. More specifically, said foaming agent is selected from sodium alginate and polyoxyethylene.

Other embodiments of the invention include multiple cleansing agents.

In another embodiment the non-adhering oral tape, film or strip home oral care composition further comprises a disintegrating agent.

Disintegrant is understood as a substance which, upon addition to a solid preparation, facilitates its break-up or disintegration after administration and permits the release of an active ingredient as efficiently as possible to allow for its rapid dissolution. As examples of the disintegrating agent, starches such as corn starch and potato starch, partial alpha starch, sodium carboxymethyl starch, carmellose, carmellose calcium, crosscarmellose sodium, polyvinyl alcohol, crospovidone, low-substituted hydroxypropyl cellulose, crystalline cellulose, hydroxypropyl starch and the like can be given. Also, hydroxypropyl cellulose may be used as a disintegrant.

In another embodiment the non-adhering oral tape, film or strip home oral care composition further comprises a spitting promoter (fiber, fibrillar network, strand, salivary stimulants, expectorants) humectants, preservatives, flavoring agents, or (sugar free) sweeteners.

Other embodiments of the invention include the non-adhering oral tape, film or strip of the invention additionally comprising at least one surfactant.

Other embodiments of the invention include the non-adhering oral tape, film or strip of the invention additionally comprising at least one vitamin, at least one polymer, at least one flavoring agent, at least one enzyme, at least one humectant, and/or at least one preservative and combinations thereof.

Other embodiments of the invention include the non-adhering oral tape, film or strip of the invention additionally comprising oil of wintergreen, oil of peppermint, oil of spearmint, oil of sassafras, oil of clove, aspartame, acesulfame, saccharin, dextrose, levulose and sodium cyclamate and combinations thereof.

In another embodiment the non-adhering oral tape, film or strip home oral care composition further comprises hydroxymethyl cellulose for the film former and additional ingredients are sodium fluoride, hydrated silica, triclosan, sodium lauryl sulphate, and PVM/MA (copolymer of methyl vinyl ether and maleic anhydride) copolymer.

In another embodiment the non-adhering oral tape, film or strip home oral care composition wherein the tape or film is in precut segments.

Another embodiment of the invention is directed to a kit comprising a non-adhering oral tape, film or strip packaged as a roll or individual layered strip in a dispenser and instructions for home use.

Another embodiment of the invention is directed to a method of using said non-adhering oral tape, film or strip comprising separating said precut segment; placing said precut segment into the oral cavity; applying agitate force to the precut segment to cleanse and fluoridate one or more teeth in the oral cavity; remove the residual precut segment from the mouth. The tape, film or strip may be contiguous laminate perforated so as to facilitate separation or as completely cut into separate segments that may be stacked in layers.

Another embodiment of the invention is directed to the use, methods, oral tape, film, strip or kits for home use particularly for children between the ages 2 and 6.

DETAILED DESCRIPTION OF THE PREFERRED EMBODIMENTS

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention.

The disclosed product comprises a film forming, liquid, preferably a water soluble polymer and a fluoridating ingredient incorporated within the polymer matrix.

Where the film forming, water soluble polymer is water soluble it may be composed of, but is not limited to polymers selected from pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, pectin, tragacanth gum, guar gum, acacia gum, Arabic gum, polyacrylic acid, methylmethacrylate copolymer, carboxyvinyl polymer, gelatin, amylase, high amylase starch, hydroxypropylated high amylase starch, dextrin, chitin, chitosan, levan, elsinan, collagen, zein, gluten, soy protein isolate, whey protein isolate, casein and mixtures thereof.

More specific film forming water soluble polymers are pullulan, hydroxypropylethyl cellulose, hydroxyethyl cellulose, hydroxypropyl cellulose, carboxymethyl cellulose, sodium alginate, pectin, and mixtures thereof.

The film forming water-soluble polymers are combined so as to form a mixture that on drying is non-adhering to wet dental surfaces. Thus starch based polymers and its derivative polymers such hydroxypropyl methyl cellulose (HPMC), hydroxypropylethyl cellulose, hydroxyethyl cellulose, hydroxypropyl cellulose, and carboxymethyl cellulose are important ingredients.

Other ingredients may be added to the blend for the purpose of stabilizing and plasticizing the film.

The film may be manufactured by conventional means and cut into various shapes.

The finished film is preferably packaged in moisture retardant packaging.

There are a variety of film formers that can be used in edible films or strips. Generally, these film formulations include the addition of a plasticizer to prevent the film from becoming too brittle and cracking or otherwise degrading during storage and handling.

There are limitations to the amount of the plasticizer that can be used in the film. When excessive plasticizer is employed, the film looses structural integrity, becomes too flimsy and significantly, becomes sticky such that it tends to adhere to other strips of film in the package forming a block. This is especially true when the strips are stacked in a vial, which is a preferred form of primary packaging.

The disclosed films solve the problems associated with high loadings of active ingredients by laminating multiple layers of thin films to one another, where the films have physical and/or chemical properties which are modified depending on the function that layer plays in the laminate structure.

This disclosure provides for the use of multiple layers to increase active loading significantly beyond single or bi-layer films. In general, there may be any number of layers of film in excess of two. For most applications, 3 to 5 layer laminates will provide the enhanced benefits.

For example, one preferred embodiment contains a bottom layer with high plasticizer content, a middle layer with a high active loading and a top layer with high plasticizer content. The resulting film lamination or sandwich remains flat and flexible even if the middle layer became brittle.

Where multiple active ingredients are desired, each may reside in its own laminate layer having different physical or chemical properties. Where two active ingredients are inter-reactive, the separate layers will significantly extend the shelf life of the product or even allow the development of new products by preventing interaction until utilized by the customer or patient.

A further embodiment anticipates that one or more of these layers may also contain air bubbles that increase surface area for improved dissolution.

These films can be manufactured individually and the multiple layers combined after manufacture but in a preferred embodiment the films are manufactured simultaneously. The simultaneous manufacturing process requires the selection of thin films that have the correct rheology so that they don't merge into one another during the manufacturing process.

Exemplary coating methods are a slot die for up to 3 layers of film slurries that have a viscosity range of approximately 15 Cp to 20,000 Cp, or a slide coater for up to 18 layers of film slurries with a viscosity range of approximately 1 Cp to 500 Cp.

Other coating methods could be used with coating layers that are not coterminious.

Toothpaste compositions contain an abrasive polishing material, typically silica but also including alumina and baking soda. Silica containing dental abrasives of various types can provide the benefits of dental cleaning and polishing performance without unduly abrading tooth enamel or dentin. Silica abrasive materials are also exceptionally compatible with sources of soluble fluoride.

Compositions may also include a humectant. The humectant serves to keep the compositions from hardening upon exposure to air. Certain humectants can also impart desirable sweetness or flavor to the compositions. Commonly used humectants include edible polyhydric alcohols such as glycerine, sorbitol, xylitol and propylene glycol.

Water is another commonly optional element of the present formulations, although as in U.S. Pat. No. 3,574,824 entitled "Anhydrous Toothpaste Formulations" water free toothpaste compositions are suitable options.

U.S. Pat. No. 5,279,815 to Wason et al. issued Jan. 18, 1994 and entitled "Dentifrice Abrasive Compositions" describe the use of calcium phosphate materials as abrasives. Compositions are also known which contain small amounts of alkaline earth metal ions, such as calcium ions, see for example U.S. Pat. No. 3,991,177, issued Nov. 9, 1976, to Vidra et al.

Vidra also describes compositions containing a stabilizer-activator for a dextranase enzyme agent with the stabilizer-activator being a salt such as calcium chloride present in an amount of 0.001 to 0.3 weight percent. Such elements are also suitable additives to the present invention.

Other literature which describes toothpaste compositions containing alkaline earth metal compounds or ions include U.S. Pat. No. 3,095,356, issued Jun. 25, 1963, to Moss; U.S. Pat. No. 3,122,483, issued Feb. 25, 1964, to Rosenthal; U.S. Pat. No. 3,669,221, issued Jun. 13, 1972, to Hase; U.S. Pat. No. 3,782,446, issued Jan. 1, 1974, to Walter; U.S. Pat. No. 3,842,168, issued Oct. 15, 1974, to Colodney; and, U.S. Pat. No. 3,689,537, issued Sep. 5, 1972, to Kuder.

Other components include sudsing agents, flavoring agents, sweetening agents, anticalculus agents, antiplaque agents, and coloring agents.

Nitrates, such as potassium nitrate, may be additionally incorporated into the present formulations desensitized the teeth during toothbrushing such as described in U.S. Pat. No. 3,863,006.

Dentifrice for desensitizing sensitive teeth wherein a potassium salt of a synthetic anionic polymer is present to close off subsequent penetration of pain to dental pulp may also be included in the present formulation. Such dentifrice includes agents such as potassium pyrophosphate and potassium nitrate; see for example U.S. Pat. No. 5,374,417 to Norfleet, et al. issued Dec. 20, 1994 and entitled "Desensitizing Dentifrice." Thus toothpastes that contain desensitizers make the teeth less painful or painless during brushing and flossing operations.

Anti-calculus (anti-tartar) agents such as tetrapotassium pyrophosphate (see U.S. Pat. No. 4,931,273) and polymeric polycarboxylates which help to prevent hydrolysis and enzymatic degradation of pyrophosphate are additional compounding agents.

While the above dentifrice compositions have been identified as illustrative of the wide range of materials useful as toothpastes usable in conjunction with the novel dissolvable thin film delivery system, this invention is not limited to the specific components of the dentifrice and is instead directed to the addition of all types of dentifrice compositions combined with the delivery system, the dissolvable polymer strip system, disclosed herein.

The dentifrice is admixed with the thin film polymer mixture before formation of the mixture into the thin strips of this invention.

The quantity of dentifrice that may be admixed will vary somewhat with the identity of the dentifrice but in general the quantity of dentifrice that may be admixed with the thin film polymer components will vary from about 1% by weight to about 35% by weight.

The dissolvable thin film toothpaste compositions of this invention are conveniently packaged as rolls in a dispenser containing a cutting surface allowing the user to cut off an appropriate length for use. Dispensers such as those used to dispense writing correction tape. One such tape dispenser is sold by Staples under the trademark OOPS! correction tape.

Example 1

Hydroxymethyl cellulose extruded as a thin film layer is coated with an extruded formulation comprising sodium fluoride, hydrated silica, triclosan, sodium lauryl sulphate, and PVM/MA (copolymer of methyl vinyl ether and maleic anhydride) copolymer and dried in an oven to form a non-adhering oral tape, film or strip home oral care composition.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

The invention claimed is:

1. A method for decreasing the risk for enamel fluorosis in a child between the ages of two to six, comprising:
   a.) providing dissolvable precut segments of an oral tape, film or strip, wherein each precut segment includes
   a film-forming water soluble polymer;
   a cleansing effective amount of a teeth cleaning agent; and
   a fluoridating agent, the fluoridating agent comprising a dosage amount of from 0.01 mg to 1 mg, wherein the fluoride concentration is about 0.004-0.008 mmoles;
   b.) placing one of said precut segments into the oral cavity of the child; and
   c.) applying agitate force to the precut segment to cleanse and fluoridate one or more teeth in the oral cavity.

2. The method according to claim 1, further comprising removing residual precut segment from the mouth.

3. The method according to claim 1, wherein said method is for home use.

4. A method for decreasing the risk for enamel fluorosis in a child between the ages of two to six for home use by said child, comprising:
   a.) providing dissolvable precut segments of an oral tape, film or strip, wherein the each precut segment includes
   a film-forming water soluble polymer comprising hydroxypropyl methyl cellulose;
   a cleansing effective amount of a teeth cleaning agent, the teeth cleaning agent comprising sodium lauryl sulfate;
   glycerine;
   a flavoring agent;
   a sweetener; and
   a fluoridating agent, the fluoridating agent comprising sodium fluoride in a dosage amount of 0.2 mg;
   b.) placing one of said precut segments into the oral cavity of the child;
   c.) applying agitate force to the precut segment to cleanse and fluoridate one or more teeth in the oral cavity; and
   d.) removing residual precut segment from the mouth.

5. The method according to claim 1, wherein the fluoride concentration is 0.006 mmoles.

6. The method according to claim 1, the fluoridating agent comprises a dosage amount of 0.2 mg.

7. The method according to claim 1, wherein each precut segment further includes glycerine, a flavoring agent and a sweetener.

8. The method according to claim 1, wherein the fluoridating agent comprises a dosage amount selected from the group consisting of 0.01 mg, 0.1 mg, 0.2 mg, 0.25 mg, 0.5 mg, 0.75 mg and 1 mg.

* * * * *